United States Patent
Luyken et al.

(10) Patent No.: US 9,828,329 B2
(45) Date of Patent: Nov. 28, 2017

(54) METHOD FOR THE DISTILLATIVE PURIFICATION OF EDA

(71) Applicant: BASF SE, Ludwigshafen (DE)

(72) Inventors: Hermann Luyken, Ludwigshafen (DE); Stephanie Jaegli, Mannheim (DE); Michael Lorenz, Ludwigshafen (DE); Gordon Brasche, Frankfurt (DE); Markus Jegelka, Mannheim (DE); Barbara Becker, Moerlenbach (DE); Robert Baumann, Mannheim (DE); Johann-Peter Melder, Boehl-Iggelheim (DE); Boris Buschhaus, Heidelberg (DE); Thomas Krug, Worms (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/125,850

(22) PCT Filed: Mar. 11, 2015

(86) PCT No.: PCT/EP2015/055028
§ 371 (c)(1),
(2) Date: Sep. 13, 2016

(87) PCT Pub. No.: WO2015/135971
PCT Pub. Date: Sep. 17, 2015

(65) Prior Publication Data
US 2017/0217874 A1  Aug. 3, 2017

(30) Foreign Application Priority Data
Mar. 13, 2014 (EP) .................... 14159511

(51) Int. Cl.
*C07C 209/84* (2006.01)
(52) U.S. Cl.
CPC ................. *C07C 209/84* (2013.01)

(58) Field of Classification Search
None
See application file for complete search history.

(56) References Cited

U.S. PATENT DOCUMENTS

| 2,571,099 A | 10/1951 | Arthur, Jr. et al. |
| 8,927,712 B2 | 1/2015 | Bou Chedid et al. |
| (Continued) | | |

FOREIGN PATENT DOCUMENTS

| DE | 1 258 413 B | 1/1968 |
| WO | WO 2004/092068 A1 | 10/2004 |
| (Continued) | | |

OTHER PUBLICATIONS https://en.wikipedia.org/wiki/Bar_(unit), 2017.*
(Continued)

*Primary Examiner* — Clinton Brooks
(74) *Attorney, Agent, or Firm* — Oblon, McClelland, Maier & Neustadt, L.L.P.

(57) ABSTRACT

The present invention relates to a process for purifying ethylenediamine (EDA) by distillation, wherein the process comprises the steps a) and b). In step a), a mixture (G1) comprising water, EDA and N-methylethylenediamine (N-MeEDA) is fed into a distillation apparatus (D1), and the major part of the water comprised in the mixture (G1) is separated off overhead at a pressure of greater than 4.8 bara. From the bottom of (D1), the water-enriched mixture (G2) is fed into a distillation apparatus (D2) in step b). At the top of (D2), the major part of the N-MeEDA is distilled off. The stream (S3) obtained from the bottom of (D2) comprises EDA, with the components water and N-MeEDA comprised in the mixture (G1) having been largely or completely removed. Further distillation steps can optionally be carried out in order to obtain pure EDA, for example when diethylenetriamine (DETA) is additionally comprised in the mixture (G1). If ammonia is additionally comprised in the
(Continued)

mixture (G1), an ammonia removal is preferably additionally carried out before carrying out the step a) in the process of the invention.

28 Claims, 2 Drawing Sheets

(56) References Cited

U.S. PATENT DOCUMENTS

| | | |
|---|---|---|
| 8,981,093 B2 | 3/2015 | Bou Chedid et al. |
| 2006/0201798 A1 | 9/2006 | Bartsch et al. |
| 2010/0087684 A1 | 4/2010 | Do et al. |
| 2010/0121109 A1 | 5/2010 | Dahmen et al. |
| 2012/0253077 A1 | 10/2012 | Jödecke et al. |
| 2013/0274522 A1 | 10/2013 | Petraitis et al. |
| 2016/0009633 A1 | 1/2016 | Luyken et al. |

FOREIGN PATENT DOCUMENTS

| | | |
|---|---|---|
| WO | WO 2008/104578 A1 | 9/2008 |
| WO | WO 2008/104579 A1 | 9/2008 |
| WO | WO 2010/042168 A2 | 4/2010 |
| WO | WO 2011/067226 A1 | 6/2011 |
| WO | WO 2012/087553 A1 | 6/2012 |

OTHER PUBLICATIONS

International Search Report dated Jun. 25, 2015 in PCT/EP2015/055028.

English translation of the International Preliminary Report on Patentability dated Sep. 15, 2016 in PCT/EP2015/055028 dated Mar. 11, 2015.

"Deuterium and Tritium (D)" Encyclopedia of Chemical Technology, 4th Edition, John Wiley & Sons, vol. 8, 1996, pp. 1-30 and Cover Page.

* cited by examiner

METHOD FOR THE DISTILLATIVE PURIFICATION OF EDA

The present invention relates to a process for purifying ethylenediamine (EDA) by distillation, wherein the process comprises the steps a) and b). In step a), a mixture (G1) comprising water, EDA and N-methylethylenediamine (N-MeEDA) is fed into a distillation apparatus (D1), and the major part of the water comprised in the mixture (G1) is separated off overhead at a pressure of greater than 4.8 bara. From the bottom of (D1), the water-enriched mixture (G2) is fed into a distillation apparatus (D2) in step b). At the top of (D2), the major part of the N-MeEDA is distilled off. The stream (S3) obtained from the bottom of (D2) comprises EDA, with the components water and N-MeEDA comprised in the mixture (G1) having been largely or completely removed. Further distillation steps can optionally be carried out in order to obtain pure EDA, for example when diethylenetriamine (DETA) is additionally comprised in the mixture (G1). If ammonia is additionally comprised in the mixture (G1), an ammonia removal is preferably additionally carried out before carrying out the step a) in the process of the invention.

Processes for preparing EDA have been known for a long time, and hydrocyanic acid is frequently used as one of the starting materials for this purpose. WO 2008/104578 discloses a process for preparing an ethylene amine mixture comprising EDA, in which crude aminoacetonitrile (crude AAN) which is largely free of formaldehyde cyanohydrin is heated at a temperature of from 50 to 150° C. This gives an amino nitrile mixture comprising AAN and iminodiacetonitrile (IDAN). This mixture is subsequently hydrogenated in the presence of a catalyst to give EDA and diethylenetriamine (DETA). It can additionally be seen from WO 2008/104578 that the crude AAN used can be obtained by reaction of an aqueous mixture of ammonia with FACH in a molar ratio of ≥4:1 [mole/mole] at a temperature of from 50 to 80° C.

The preparation of formaldehyde cyanohydrin (FACH) has likewise been known for a long time. Detailed information on the preparation of FACH from formaldehyde and hydrocyanic acid may be found, for example, in WO 2008/104579. However, in this process the FACH is not used for preparing EDA via AAN by reaction with ammonia, but instead FACH is reacted with EDA to give ethylenediaminediacetonitrile (EDDN). EDDN can in turn be hydrogenated to triethylenetetraamine (TETA).

WO 2011/067226 relates to a process for distilling a mixture comprising water, ethylenediamine and N-methylethylenediamine, in which the mixture is fed into a distillation column which is operated at a pressure at the top of from 10 mbar to 4 bar. Water and ethylenediamine have to be present in a specific ratio in this mixture. The mixture used for the distillation is in turn a reaction product which can be obtained by reaction of formaldehyde, hydrocyanic acid, ammonia and hydrogen or by reaction of ethylene oxide with ammonia to form ethanolamine and the further reaction of ethanolamine with ammonia.

Furthermore, it is known from WO 2011/067226, page 2, lines 13 to 14, that EDA and N-MeEDA form a close-boiling azeotropic mixture at atmospheric pressure, and this generally cannot be separated with an industrially justifiable outlay. In WO 2011/067226, the separation of N-methylethylenediamine from ethylenediamine is carried out by separating off an N-methylethylenediamine/water azeotrope at the top of a column. In some embodiments of the process of WO 2011/067226, water even has to be additionally introduced into the process in order to make the azeotropic removal of the N-MeEDA/water mixture possible. In the corresponding column, ever greater amounts of water remain at the bottom of the column and these have to be additionally separated from the target product EDA in subsequent distillation steps.

Furthermore, it is known from DE-A 1 258 413 that EDA forms an azeotropic mixture having a boiling point of about 118° C. with water at atmospheric pressure. The azeotrope consists of 82% of EDA and 18% of water and has a boiling point about 2° C. higher than that of pure EDA (116° C.). With increasing pressure, the EDA content of the azeotrope increases. Above 4.8 bar, an azeotrope no longer exists.

WO 2010/042168 describes a process for preparing ethylenediamine from ethylene oxide and ammonia via the intermediate ethanolamine. The crude ethylenediamine formed in the reaction of ethanolamine with ammonia comprises the by-products N-ethylethylenediamine and N-methylethylenediamine. In example 3 and FIG. 4, it is shown how the two N-alkylethylenediamines can be separated off from ethylenediamine by azeotropic distillation.

A disadvantage of the processes of WO 2010/042168 and WO 2011/067226 is that the azeotropic distillations form not inconsiderable amounts of wastewater and the nitrogen compounds comprised therein have to be, for example, degraded in a water treatment plant.

The process described in WO 2011/067226 for separating ethylenediamine and N-methylethylenediamine has disadvantages particularly when the ratio of water to ethylenediamine in the feed stream is lower than in the binary azeotrope and the mixture comprises a large amount of N-methylethylenediamine. In this case, additional water has to be added to the feed stream of the column (see WO 2011/067226, example 4). Since this water has to be separated off again, this embodiment is not very advantageous.

A further disadvantage is that the water content has to be set precisely before the distillation in order to avoid EDA losses via the top of the column.

The object of the present invention is therefore to provide a novel process for purifying ethylenediamine (EDA).

The object is achieved by a process for purifying ethylenediamine (EDA) by distillation, which comprises the step a) and b), namely:
a) introduction of a mixture (G1) comprising water, EDA and N-methylethylenediamine (N-MeEDA) into a distillation apparatus (D1), with
   i) a stream (S1) comprising water being distilled off overhead from (D1) at a pressure of greater than 4.8 bara and
   ii) a mixture (G2) depleted in water compared to the mixture (G1) being taken off from the bottom of (D1),
b) introduction of the mixture (G2) into a distillation apparatus (D2), with
   (i) a stream (S2) comprising N-MeEDA being distilled off overhead from (D2) and
   ii) a stream (S3) depleted in N-MeEDA compared to the mixture (G2) being taken off from the bottom of (D2).

A substantial advantage of the process of the invention is that no azeotropic separations of water with N-MeEDA and/or with EDA have to be carried out. Instead, the major part of the water comprised in the feed mixture is firstly separated off from EDA in a first process step according to the invention without an azeotropic removal of water occurring. In a second process step, N-MeEDA is subsequently separated off from EDA, again not under azeotropic conditions.

A further advantage of the process of the invention is that the process can be carried out very variably. The EDA to be purified can be used independently of the specific production route; in principle, EDA can be prepared by all processes known to those skilled in the art. For example, the EDA can be prepared from formaldehyde and hydrocyanic acid or using ethylene oxide and ammonia. In the processes known from the prior art, appreciable amounts of wastewater are obtained. Owing to the azeotropic separation conditions, the water separated off generally comprises a large proportion of nitrogen compounds as secondary components (i.e. EDA, DETA, N-MeEDA, etc.). This wastewater therefore has to be additionally purified in a water treatment plant.

Water does also have to be separated off according to the invention. If EDA is prepared from aqueous, 20-60% strength formaldehyde, even relatively large amounts of water which has to be separated off are generally comprised in the mixture (G1) to be fractionated. However, owing to the process conditions in step a) of the process of the invention, very small amounts of nitrogen-comprising compounds are present in the water separated off, so that the outlay for purification is lower.

A further advantage of the process of the invention is that the N-MeEDA which is obtained as overhead product in step b) and can also be present as a mixture with EDA can be advantageously used as component for preparing epoxy resins.

If the EDA comprised in the mixture (G1) used in the process of the invention is prepared using hydrocyanic acid which is completely free or largely free of sulfur dioxide ($SO_2$), a further advantage of the process of the invention is that the operating life of the hydrogenation catalyst (i.e. of the catalyst used in step A3) as per process A) is improved. This effect occurs particularly when the hydrocyanic acid used for the preparation of FACH as per step A1) is completely or at least largely free of sulfur dioxide and also of any further acidic stabilizers such as sulfuric acid or phosphoric acid.

The use of (largely) $SO_2$-free hydrocyanic acid in step A3) thus has a particularly positive effect on the performance of the hydrogenation catalyst used in step A3). The AAN hydrogenation can thus be carried out over long times with high EDA yields without a significant reduction in the catalyst activity. In particular $SO_2$ tends to disproportionate in the presence of the catalyst under the process conditions customary in a nitrile hydrogenation, forming, inter alia, sulfides which contribute significantly to reducing the performance of a hydrogenation catalyst. In contrast, such disproportionation is not observed or observed only to a significantly reduced extent when sulfuric acid is used instead of $SO_2$.

Figure 1:
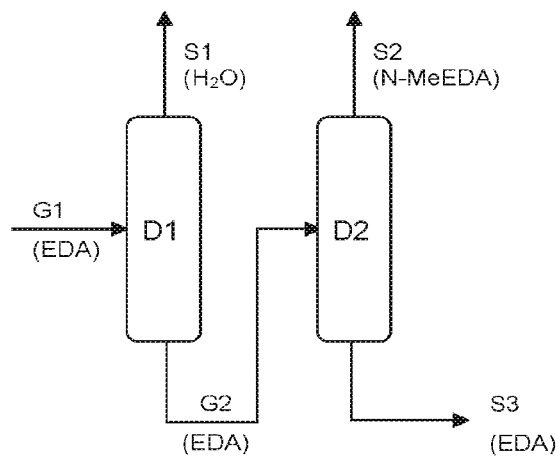
FIG. 1 shows a process of the invention in its basic form.

The present invention is explained in more detail below.

In step a) of the process of the invention, a mixture (G1) comprising water, EDA and N-methylethylenediamine (N-MeEDA) is fed into a distillation apparatus (D1), with i) a stream (S1) comprising water being distilled off overhead from (D1) at a pressure of greater than 4.8 bara and ii) a mixture (G2) depleted in water compared to the mixture (G1) being taken off from the bottom of (D1).

The components water, EDA and N-MeEDA comprised in the mixture (G1) in step a) are known per se to those skilled in the art. In one embodiment of the present invention, the mixture (G1) comprises essentially, preferably to an extent of at least 99% by weight, EDA, N-MeEDA and water. As described in more detail below, further components such as diethylenetriamine (DETA) or ammonia ($NH_3$) can also be comprised in the mixture (G1). Such additional components are preferably (as likewise described in more detail below) separated off from the corresponding mixture either before carrying out step a), as in the case of ammonia, or after step b), as in the case of DETA.

The individual components of the mixture (G1) can in principle be present in any ratios relative to one another.

In one embodiment of the present invention, the mixture (G1) comprises essentially, preferably to an extent of at least 99% by weight, in particular at least 99.5% by weight, EDA, N-MeEDA, DETA, water and $NH_3$. In this embodiment, the ammonia is preferably completely or at least largely removed from the mixture (G1) before carrying out the step a) according to the invention.

The distillation apparatus (D1) used in step a) of the process of the invention can in principle be any distillation apparatus known for this purpose to a person skilled in the art, for example a column. The specific configuration of the distillation apparatus (D1) is explained below in the present text.

The separation according to the invention of the water from N-methylethylenediamine or the water from EDA is achieved when the distillation is carried out at a pressure above 4.8 bar. Under these conditions, no ethylenediamine/water azeotrope or N-methylethylenediamine/water azeotrope exists.

As explained in more detail below, it is possible, for example, for the reaction output from the hydrogenation of aminoacetonitrile or the reaction of ethanolamine with ammonia firstly to be freed of ammonia in the distillation apparatuses (D1) and (D4). The reaction output from the distillation apparatus (D4) can thus be fed into the distillation apparatus (D1) in order to separate off water.

According to the invention, the water is largely or completely separated off at the top of the distillation apparatus (D1). For the purposes of the present invention, the term "largely free of water" or "substantial removal of the water" means the following: the amount of water remaining in the bottom product from the distillation apparatus (D1) is less than 1000 ppm by weight, preferably less than 200 ppm by weight, in particular less than 50 ppm by weight.

A reaction mixture (G2) comprising essentially ethylenediamine, N-methylethylenediamine and possibly diethylenetriamine is obtained as bottom product from the distillation apparatus (D1).

The pressure at the top of the distillation apparatus (D1) is preferably from >4.8 to 20 bar, more preferably from 5 to 10 bar, particularly preferably from 5 to 6 bar.

The temperature at the bottom of the distillation apparatus (D1) is preferably from 175 to 250° C., more preferably from 175 to 220° C., particularly preferably from 180 to 200° C.

The water separated off preferably comprises less than 1% by weight, more preferably less than 1000 ppm by weight, particularly preferably less than 100 ppm by weight, of nitrogen in the form of organic nitrogen compounds, especially in the form of amines.

In a preferred embodiment, the temperature at the bottom of the distillation apparatus (D1) in step a) is from 175 to 250° C. and/or the water present in the mixture (G1) is completely or at least largely distilled off overhead from (D1). Furthermore, preference is given in this embodiment to the mixture (G2) taken off from the bottom of the distillation apparatus (D1) in step a) comprising less than 1000 ppm by weight of water, more preferably less than 200 ppm by weight of water, in particular less than 50 ppm by weight of water.

In step b), the mixture (G2) is fed into a distillation apparatus (D2), with i) a stream (S2) comprising N-MeEDA being distilled off overhead from (D2) and ii) a stream (S3) depleted in N-MeEDA compared to the mixture (G2) being taken off from the bottom of (D2).

N-Methylethylenediamine which preferably comprises from 20 to 50 ppm by weight, more preferably from 22 to 40 ppm by weight, particularly preferably from 23 to 30 ppm by weight, of ethylenediamine is taken off as overhead product from the distillation apparatus (D2).

A mixture of ethylenediamine and possibly diethylenetriamine, which preferably comprises from 0 to 10 000 ppm, more preferably from 0 to 1000 ppm, particularly preferably from 0 to 200 ppm, of N-methylethylenediamine (ppm by weight) goes out at the bottom of the distillation apparatus (D2).

The temperature at the bottom of the distillation apparatus (D2) is preferably from 20 to 75° C., more preferably from 40 to 70° C., particularly preferably from 55 to 65° C.

The pressure at the top of the distillation apparatus (D2) is preferably from 10 to 500 mbar, more preferably from 30 to 300 mbar, particularly preferably from 50 to 200 mbar.

The distillation apparatus (D2) normally comprises from 50 to 200 theoretical plates, preferably from 70 to 150 theoretical plates, particularly preferably from 80 to 120 theoretical plates. Preference is given to low-pressure-drop packings.

The ratio of amount of runback to amount of feed is normally from 0.5 to 100, preferably from 2.0 to 10, particularly preferably from 3.0 to 5.

From 0.02 to 0.04 kg of N-methylethylenediamine are preferably obtained per kg of ethylenediamine and are separated off in step b) according to the invention.

In a preferred embodiment of the present invention, the distillation apparatus (D2) is operated at a temperature at the bottom of from 20 to 75° C. and/or at a pressure at the top of from 10 to 500 mbara, in particular from 50 to 200 mbara, in step b). Furthermore, preference is given in this embodiment to the stream (S3) taken off from the bottom of the distillation apparatus (D2) in step b) comprising less than 10 000 ppm by weight of N-MeEDA, more preferably less than 1000 ppm by weight of N-MeEDA, in particular less than 200 ppm by weight of N-MeEDA. Preference is likewise given in this embodiment to the stream (S2) distilled off overhead from the distillation apparatus (D2) in step b) comprising from 20 to 50 ppm by weight of EDA, more preferably from 22 to 40 ppm by weight of EDA, in particular from 23 to 30 ppm by weight of EDA.

If the mixture (G1) additionally comprises ammonia ($NH_3$), a removal of ammonia from the mixture (G1) is preferably carried out in step c) before step a).

Step c) is preferably carried out in two stages, wherein
in the first stage, ammonia is taken off overhead at from 20 to 70° C. from the mixture (G1) in a distillation apparatus (D3) and is condensed, the temperature at the bottom is less than 220° C. and a mixture (G1a) depleted in $NH_3$ is transferred from the bottom to a distillation apparatus (D4),
in the second stage, the mixture (G1b) is separated off from the bottom in the second distillation apparatus (D4), with the mixture (G1b) being (largely) free of ammonia and the mixture (G1b) being fed instead of the mixture (G1) into the distillation apparatus (D1) in step a).

As distillation apparatuses (D3) and (D4), it is possible to use all distillation apparatuses known for this purpose to a person skilled in the art. In the distillation apparatus (D3), the temperature at the top of the column ("condensation temperature") is preferably from 20 to 70° C., in particular from 35 to 60° C. The temperature in the distillation apparatus (D3), in particular in the top region, is preferably regulated via the pressure. The pressure can be determined with the aid of vapor pressure tables for ammonia known to those skilled in the art. The temperature at the bottom of the distillation apparatus (D3) is preferably <200° C., particularly preferably <190° C. The temperature at the bottom is preferably set via the ammonia content which is taken off from the bottom of the distillation apparatus (D3). In general, the temperature at the bottom does not go below 140° C.

In the second stage, the column pressure is preferably set in such a way that the bottom output from the distillation apparatus (D4) is free or largely free of ammonia. The bottom output is considered to be largely free of ammonia when the ammonia content is <1% by weight, preferably <0.5% by weight, and the bottom output is considered to be free of ammonia when the ammonia content is <0.1% by weight, preferably 0.01% by weight.

The temperatures at the bottom of the distillation apparatus (D4) correspond to the temperatures at the bottom which have been indicated above in connection with the distillation apparatus (D3). Ammonia is separated off from the upper part of the distillation apparatus (D4), preferably via the top of the column. This stream preferably comprises water in addition to ammonia. Here, the water content is preferably set so that the temperature at the top of the distillation apparatus (D4) or the condensation temperature corresponds to the temperature ranges at the top of the column indicated above for the distillation apparatus (D3). The $NH_3$-comprising stream which is preferably taken off from the top of the column of (D4) and additionally comprises water is preferably recirculated to the first stage of ammonia removal in the distillation apparatus (D3). The condenser is particularly preferably in the form of a closed condensation. This can be effected by backmixing of the condensate (introduction of a circulating stream via the condenser) or by condensation in cocurrent.

Furthermore, preference is given in the process of the invention to EDA comprised in the mixture (G1) being prepared by a process (A) or a process (B), wherein the process (A) comprises the steps (A1) to (A3):
A1) reaction of formaldehyde and hydrocyanic acid (HCN) to form formaldehyde cyanohydrin (FACH), where the hydrocyanic acid is completely or largely free of sulfur dioxide ($SO_2$), A2) reaction of FACH with ammonia (NH$_3$) to form aminoacetonitrile (AAN), A3) hydrogenation of AAN in the presence of a catalyst to give EDA, and the process (B) comprises the steps (B1) and (B2):

B1) reaction of ethylene oxide (EO) with ammonia (NH$_3$) to form ethanolamine (EOA), B2) reaction of EOA with NH$_3$ to form EDA.

The above-described processes (A) and (B) are known per se to those skilled in the art. Furthermore, preference is given to the EDA used in the process of the invention being, insofar as it has been prepared by one of the two above-described processes, subjected directly after the hydrogenation of AAN as per step A3) or the reaction of EOA as per step B2) to a removal of ammonia, preferably as described above.

Furthermore, the EDA comprised in the mixture (G1) is, in the process of the invention, prepared by the above-described process (A) comprising the steps A1) to A3). The process (A) is explained in more detail in the following text.

In the process of the invention, formaldehyde and hydrocyanic acid (HCN) are reacted to form formaldehyde cyanohydrin (FACH) in step A1), with the hydrocyanic acid being completely or largely free of sulfur dioxide (SO$_2$).

Formaldehyde is a chemical which is generally availably commerce. Formaldehyde is preferably used in the form of an aqueous solution. This is preferably aqueous formaldehyde having a formaldehyde content of from 20 to 60% by weight [mole/mole], particularly preferably having a formaldehyde content of from 25 to 55% by weight.

Hydrocyanic acid is likewise a chemical which is generally available in commerce. Hydrocyanic acid can be prepared industrially by essentially three different processes. In a first process, hydrocyanic acid can be obtained by ammoxidation of methane by means of oxygen and ammonia (Andrussow process). In a second process, hydrocyanic acid can be obtained from methane and ammonia by ammondehydrogenation in the absence of oxygen. Finally, hydrocyanic acid can be prepared industrially by dehydration of formamide.

Hydrocyanic acid can be used in liquid or gaseous form, in pure form or as an aqueous solution. Hydrocyanic acid is preferably used as a from 50 to 100% strength by weight aqueous solution, particularly preferably as a from 75 to 100% strength by weight aqueous solution. Hydrocyanic acid is preferably used in a purity of 90% by weight or more.

As indicated above (including the specific numerical values), the hydrocyanic acid can be completely or largely free of sulfur dioxide (SO$_2$) in the process of the invention. Sulfur dioxide can be added directly as stabilizer to the hydrocyanic acid (for example after the preparation thereof). A person skilled in the art will know that SO$_2$ forms sulfurous acid (H$_2$SO$_3$) in the presence of water. Measurement methods for determining the SO$_2$ content of hydrocyanic acid are known to those skilled in the art; for example, this can be carried out by ion chromatography.

Since stabilizers, in particular acidic stabilizers, are generally comprised in commercially available hydrocyanic acid, the present invention is carried out using either freshly synthesized and thus stabilizer-free hydrocyanic acid or the stabilizers present, in particular sulfur dioxide, are removed by methods known to those skilled in the art immediately before use in step A1). Stabilizer-free hydrocyanic acid can be produced by distillation from hydrocyanic acid comprising nonvolatile stabilizers, in particular sulfuric acid or phosphoric acid, using the methods described in WO 2004/092068. In this case, hydrocyanic acid is distilled off overhead and the respective stabilizers are obtained as bottom products.

Stabilizer-free hydrocyanic acid can be obtained from hydrocyanic acid comprising volatile stabilizers, in particular sulfur dioxide, by passing an inert gas through the hydrocyanic acid, as described in U.S. Pat. No. 2,571,099.

In a preferred embodiment of the present invention, step A1) is carried out using hydrocyanic acid which is completely or largely free of stabilizers. The corresponding numerical values for the terms "completely free" and "largely free" have been defined above. In the context, stabilizers are considered to be, in particular, sulfur dioxide, sulfuric acid, phosphoric acid, acetic acid, oxalic acid and any other acids which are known to those skilled in the art as acidic stabilizers for hydrocyanic acid.

The reaction of formaldehyde, preferably aqueous formaldehyde, and hydrocyanic acid for forming FACH can be carried out batchwise, semicontinuously or continuously. It is preferably carried out in a backmixed reactor with removal of heat, for example using a heat exchanger. As reactors for carrying out step A1), it is possible to use, in particular, stirred reactors, loop reactors or tube reactors.

Step A1) can in principle be carried out at any temperature, but the reaction temperature is preferably from 0 to 70° C., more preferably from 10 to 50° C., particularly preferably from 20 to 45° C.

The pressure in step A1) is selected so that the reaction mixture is present in the liquid state.

The hydrocyanic acid is preferably used in an equimolar amount or a slight excess relative to formaldehyde. The molar ratio of HCN to formaldehyde is more preferably 0.85-1.0:1 [mole/mole], even more preferably 0.9-1.0:1 [mole/mole], in particular 0.95-1.0:1 [mole/mole].

Furthermore, the reaction mixture is preferably brought to a pH of from 3.5 to 6.5, more preferably from 4.0 to 6.0, particularly preferably 5.5, by means of a base, preferably sodium hydroxide.

The residence time in the FACH synthesis is from 1 minute to 1 hour, preferably from 5 minutes to 30 minutes.

The HCN conversion in the FACH synthesis is >99% (determined by Volhard titration), and the FACH yield is >98% (determined by combined Volhard and Liebig titration).

If the (preferably aqueous) FACH solution obtained is, for example, to be concentrated to give a 50-80% strength by weight solution, it is advantageous to reduce the pH in the reaction mixture of step A1) to values of <5.5, preferably <3.5. This can be achieved, for example, by addition of mineral acids such as sulfuric acid or phosphoric acid.

In step A2) of the process of the invention, FACH is reacted with ammonia (NH$_3$) to form aminoacetonitrile (AAN).

According to the invention, the reaction output from step A1), i.e. the FACH or a mixture comprising FACH, is generally reacted, without work-up and without the additional use of a solvent, with ammonia to form AAN. In step A2), ammonia can be used not only as starting material in the preparation of AAN but also as solvent. An aqueous FACH solution obtained in step A1) can optionally be concentrated by evaporation of water.

The reaction of FACH with ammonia can be carried out batchwise, semicontinuously or continuously. The reaction can be carried out in any suitable apparatus known to those skilled in the art. An adiabatic or cooled flow tube without backmixing or a reactor having plugged flow characteristics is preferably used in step A2). In this way, the formation of interfering secondary components from FACH and AAN, recognizable by the color, can be avoided.

In step A2) the temperature is generally from 0 to 150° C., preferably from 50 to 100° C., particularly preferably from 70 to 90° C.

The pressure in step A2) can in principle be set to any desired value. The pressure in step A2) is preferably from 20 to 400 bar, in particular from 80 to 270 bar. The pressure in step A2) is preferably so high that the reaction mixture is in the liquid state. Furthermore, the pressure in step A2) is preferably higher than that in step A3). For example, the pressure in step A2) can be from 5 to 20 bar higher than that in step A3).

The molar ratio of FACH to ammonia can have any desired value, but it is usual to use at least an equimolar amount of ammonia, preferably a slight molar excess of ammonia over FACH. In step A2), the molar ratio of FACH to ammonia is preferably from 1:2 to 1:15 [mole/mole], more preferably from 1:5 to 1:30 [mole/mole], in particular from 1:10 to 1:20 [mole/mole].

The residence time of the reaction mixture in the respective apparatus is preferably from 0.1 to 20 minutes, particularly preferably from 1.0 to 10 minutes.

The AAN yield is (based on FACH) preferably 95%. Furthermore, the weight ratio of AAN to IDAN is preferably ≥99:1.

In step A2), the reaction output preferably comprises from 10 to 50% by weight of AAN, from 10 to 80% by weight of ammonia, <1% by weight of FACH, <1% by weight of IDAN. The balance is water which is formed in step A2) in the preparation of AAN or has already been introduced together with the starting materials in the preparation of FACH.

In a preferred embodiment of the present invention, the AAN obtained in step A2) is i) hydrogenated as crude AAN in step A3) without work-up by distillation and/or removal of water or ii) subjected to adsorptive purification using an ion exchanger or a metal oxide before being hydrogenated in step A3).

In step A3) of the process of the invention, the hydrogenation of AAN is carried out in the presence of a catalyst to give ethylenediamine (EDA).

The hydrogenation to give EDA is generally carried out by reacting AAN with hydrogen in the presence of the catalyst ("hydrogenation catalyst"). Here, at least two mol of hydrogen are required per mole of AAN. The AAN obtained in step A2) can be subjected directly to the hydrogenation in step A3) but work-up steps can optionally be carried out between step A2) and step A3), as explained in more detail below.

The hydrogen is generally used in the form of industrial purity hydrogen. However, the hydrogen can also be used in the form of a hydrogen-comprising gas, i.e. with accompanying amounts of other inert gases such as nitrogen, helium, neon, argon or carbon dioxide. As hydrogen-comprising gases, it is possible to use, for example, reformer offgases, refinery gases, etc., when and insofar as these gases do not comprise any catalyst poisons for the hydrogenation catalysts used, for example, CO.

However, preference is given to using pure hydrogen or essentially pure hydrogen in the process, for example hydrogen having a content of more than 99% by weight of hydrogen, preferably more than 99.9% by weight of hydrogen, particularly preferably more than 99.99% by weight of hydrogen, in particular more than 99.999% by weight of hydrogen.

As catalysts, it is in principle possible to use all catalysts known to those skilled in the art for a nitrile hydrogenation. It is thus possible to use, for example, catalysts which comprise one or more elements of transition group 8 of the Periodic Table (Fe, Co, Ni, Ru, Rh, Pd, Os, Ir, Pt), preferably Fe, Co, Ni, Ru or Rh, particularly preferably Co or Ni, as active species as catalysts for the hydrogenation (hydrogenation catalysts) of the nitrile function of AAN.

These include skeletal catalysts (also referred to as Raney® type; hereinafter also: Raney catalyst) which are obtained by leaching (activation) of an alloy of the hydrogenation-active metal and a further component (preferably Al). The catalysts can additionally comprise one or more promoters.

In a particularly preferred embodiment, the hydrogenation of AAN is carried out using Raney catalysts, preferably Raney cobalt or Raney nickel catalysts and particularly preferably a Raney cobalt catalyst comprising at least one of the elements Ni, Cr or Fe as promoter. The Raney cobalt catalyst is thus doped with at least one of these elements. According to the invention, the Raney catalysts are preferably used as suspended Raney catalysts.

The catalysts can be used in the form of all-active catalysts or in supported form. Supports employed are preferably metal oxides such as $Al_2O_3$, $SiO_2$, $ZrO_2$, $TiO_2$, mixtures of metal oxides or carbon (activated carbons, carbon blacks, graphite).

In a preferred embodiment of the present invention, $NH_3$ is separated off in the optional step c) and recirculated to a preceding process step; the recirculation of ammonia is preferably carried out to a point downstream of step A2) of process (A) or to a point downstream of at least one of the two steps B1) or B2) of process (B).

Furthermore, the process of the invention preferably comprises an additional step d):

d) introduction of the stream (S3) into a distillation apparatus (D5), with EDA being distilled off overhead from D5 at a pressure of from 200 mbara to 2 bara and the EDA preferably having a purity of at least 95%, more preferably at least 99%, in particular at least 99.5%.

The temperature at the bottom of the distillation apparatus (D5) is normally from 150 to 250° C., preferably from 170 to 220° C., particularly preferably from 175 to 185° C.

The pressure at the top of the distillation apparatus (D5) is normally from 200 mbar to 2 bar, preferably from 250 mbar to 500 mbar, particularly preferably from 250 mbar to 350 mbar.

If diethylenetriamine (DETA) is additionally comprised in the mixture (G1) in the process of the invention, a DETA removal is carried out as additional step e) according to the invention; the step e) is preferably carried out after step b) and/or step d) and particular preference is given to the sequence of steps b), d), e).

Furthermore, preference is given to DETA being present in stream (S3) and a stream (S4) enriched in DETA being taken off from the bottom of the distillation apparatus (D5) and the step e) being carried out as follows:

e) introduction of the stream (S4) into a distillation apparatus (D6), with DETA being distilled off via a side offtake from D6.

The temperature at the bottom of the distillation apparatus (D6) is normally from 100 to 250° C., preferably from 170 to 220° C., particularly preferably from 175° C. to 200° C.

The pressure at the top of the distillation apparatus (D6) is normally from 10 to 500 mbar, preferably from 20 to 100 mbar, particularly preferably from 30 to 60 mbar.

In addition, low boilers remaining as overhead product and/or high boilers remaining as bottom product can optionally be separated off from the distillation apparatus (D6).

The distillations carried out in the process of the invention using the above-described distillation apparatuses (D1) to (D6) can be carried out in any suitable apparatus known to those skilled in the art. Apparatuses as are described, for example, in: Kirk-Othmer, Encyclopedia of Chemical Technology, 4th edition, vol. 8, John Wiley & Sons, New York, 1996, pages 334 to 348, for example sieve tray columns, bubble cap tray columns comprising ordered packing, columns packed with random packing elements or single-stage evaporators such as falling film evaporators, thin film evaporators, flash evaporators, multiphase helical tube evaporators, natural convection evaporators or forced circulation flash evaporators, are suitable for these distillations.

The distillation columns (D1) to (D6) preferably have internals for increasing the separation power. The distillation internals can, for example, be present as ordered packing, for example as sheet metal packing such as Mellapak 250 Y or Montz Pak, type B1-250. It is also possible for packing having a lower or increased specific surface area to be present, or a mesh packing or a packing having a different geometry, e.g. Mellapak 252 Y, can be used. Advantageous when these distillation internals are used are the low pressure drop and the low specific liquid holdup compared to, for example, valve trays. The internals can be present in one or more beds.

The number of theoretical plates in the distillation apparatus (D1) is from 50 to 100, preferably from 55 to 70, particularly preferably from 60 to 65, that in the distillation apparatus (D2) is from 70 to 150, preferably from 80 to 120, particularly preferably from 90 to 110, but in the distillation apparatus (D5) is from 15 to 50, preferably from 20 to 40, particularly preferably from 23 to 30, and that in the distillation apparatus (D6) is from 5 to 30, preferably from 7 to 20, particularly preferably from 8 to 15.

The process of the invention in its basic form is shown once more in FIG. 1. The most important components comprised in the respective mixture streams are shown in brackets under the mixtures or streams.

Figure 2:
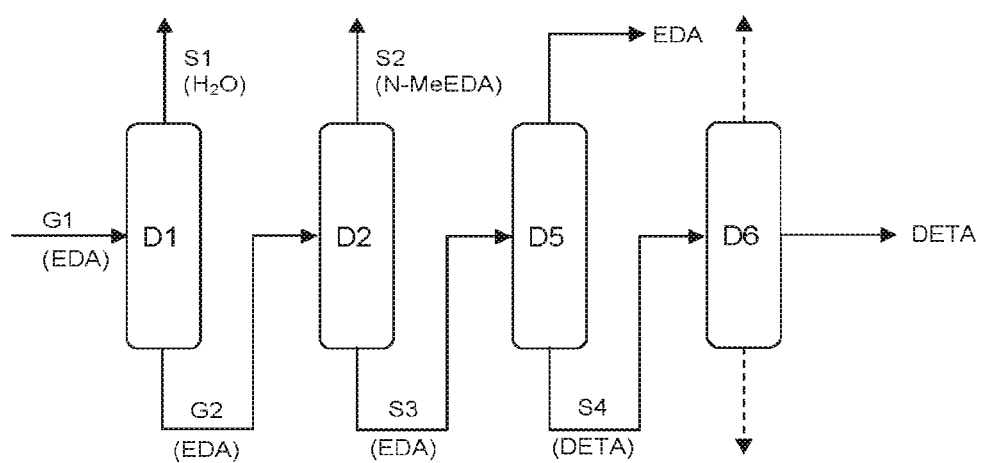
FIG. 2 shows an embodiment of the present invention. Compared to the embodiment as per FIG. 1, the embodiment as per FIG. 2 additionally comprises an EDA isolation via the distillation apparatus (D5) and a DETA removal via the distillation apparatus (D6).

A preferred embodiment of the present invention is additionally shown in FIG. 2. In FIG. 2, the abbreviations, arrows and other symbols have an analogous meaning to those in FIG. 1. Compared to the embodiment as per FIG. 1, the embodiment as per FIG. 2 additionally comprises an EDA isolation via the distillation apparatus (D5) and a DETA removal via the distillation apparatus (D6). DETA is here obtained via a side offtake from (D6). The broken lines mean that further components such as stream (S4) can optionally be comprised, and these can be separated off via the top and/or the bottom of (D6).

Figure 3:
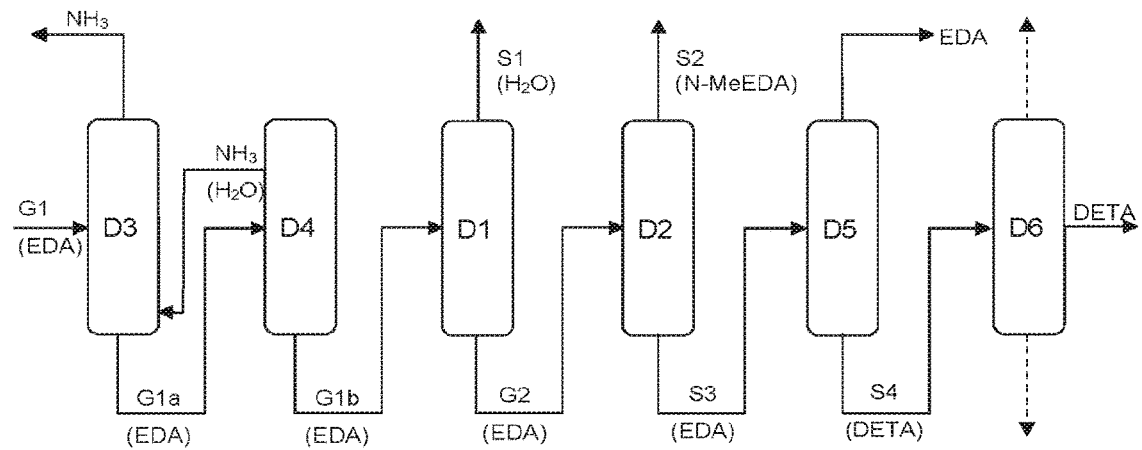
FIG. 3 shows a preferred embodiment of the present invention. In this embodiment, an ammonia removal as per step c) is carried out before carrying out the step a) according to the invention.

A further preferred embodiment of the present invention is additionally shown in FIG. 3; here, reference is made to what has been said above in respect of the FIGS. 1 and 2. In this embodiment, an ammonia removal as per step c) is carried out before carrying out the step a) according to the invention. As can be seen from FIG. 3, the ammonia removal comprises two stages using distillation apparatuses (D3) and (D4). In this embodiment, ammonia is thus additionally comprised in the feed mixture (G1). Consequently, the mixture (G1d) is fed instead of the mixture (G1) into the distillation apparatus (D1) in step a) of the process of the invention.

Figure 4:
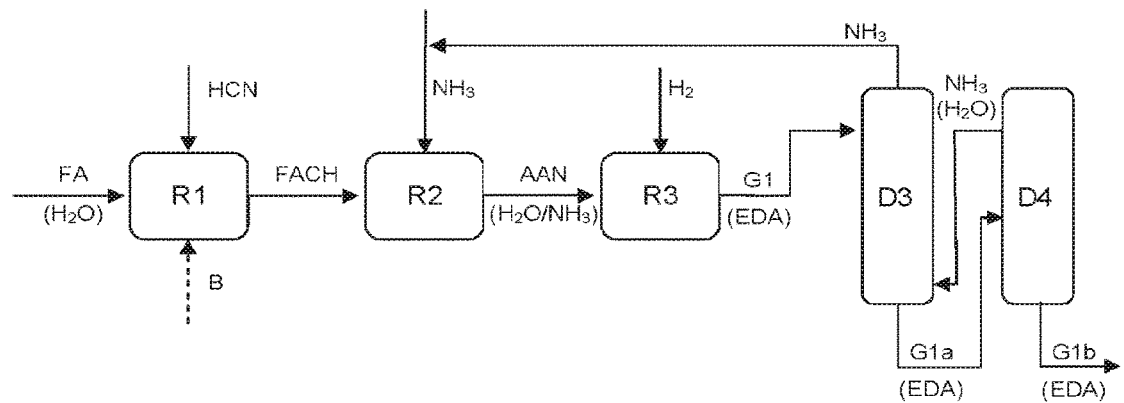
FIG. 4 shows a preferred embodiment of the present invention. In this embodiment, the EDA comprised in the mixture (G1) is prepared as in the above-described process (A) and a two-stage ammonia removal from the mixture (G1) is additionally carried out after the hydrogenation as per process (A3), in a manner analogously to the above-described embodiment as per FIG. 3.

A further preferred embodiment of the present invention is additionally shown in FIG. 4. In this embodiment, the EDA comprised in the mixture (G1) is prepared as in the above-described process (A) and a two-stage ammonia removal from the mixture (G1) is additionally carried out after the hydrogenation as per process (A3), in a manner analogously to the above-described embodiment as per FIG. 3. "FA" is short for formaldehyde, and "B" is short for base. The use of a base here is merely optional, as is indicated by the broken line. The process steps (A1) to (A3) are preferably carried out in the corresponding reactors designated analogously as "R1" to "R3" in FIG. 4. The main components (starting materials or products) of the steps (A1) to (A3) are indicated correspondingly using arrows; the most important by-products and unreacted starting materials in the individual steps are indicated in brackets.

FIG. 4 thus shows only a subregion of this embodiment of the process of the invention; the mixture (G1b) obtained from the distillation apparatus (D4) is subsequently subjected to at least the steps a) and b) according to the invention, as depicted in FIG. 1. Likewise, the additional process steps comprised in the embodiment as per FIG. 2 can also be carried out together with the distillation apparatuses (D5) and (D6). This is, in particular, the case when appreciable amounts of DETA are comprised in the mixture (G1). The embodiment depicted in FIG. 4 is particularly preferably carried out as a combination with the embodiment as per FIG. 2.

The invention is illustrated below with the aid of the examples.

EXAMPLE 1: PRELIMINARY AMMONIA REMOVAL 45.0 kg/h of a stream (mixture G1) comprising 64.1% of $NH_3$, 21.4% of $H_2O$, 13.3% of EDA, 0.35% of N-MeEDA, 0.46% of DETA and 0.39% of unknown secondary components are fed to a stripping column D3 having 3 theoretical points which are operated at 18.0 $bar_{abs}$. A temperature of 180° C. is set at the bottom of D3. The overhead output from the subsequent column D4 is fed into the bottom of D3. This stream consists of 3.17 kg/h comprising 31.2% of $NH_3$, 58.9% of $H_2O$, 9.1% of EDA, 0.56% of N-MeEDA, 430 ppm of DETA, balance miscellaneous.

In D3, 28.9 kg/h of $NH_3$ with 0.2% of $H_2O$ are taken off overhead. At the bottom, 19.29 kg/h comprising 5.6% of NH3, 59.3% of $H_2O$, 32.3% of EDA, 0.905% of N-MeEDA, 1.08% of DETA and 0.87% of miscellaneous are taken off. The temperature at the bottom is 180° C.

The bottom output from D3 is conveyed into a column D4 having a stripping section having 13 theoretical plates. D4 is operated at a pressure of 9.0 $bar_{abs}$. A mixture which is condensed by circulation over a heat exchanger at 69° C. is taken off overhead. The overhead output is recirculated to the column D3 as described above. The temperature at the bottom of D4 is 183° C. At the bottom, a mixture (mixture G1 b) comprising less than 10 ppm of $NH_3$ and 59.7% of $H_2O$, 37.0% of EDA, 0.98% of N-MeEDA, 1.30% of DETA and 1.0% of miscellaneous components is discharged.

EXAMPLE 2

The bottom output from D4 in example 1 is dewatered by being fed into a column D1 having 60 theoretical plates, viz. 32 in the stripping section and 28 in the enrichment section. D1 is operated at a pressure of 5.4 bar abs, the temperature at the top is 154.8° C. and the temperature at the bottom is 182.5° C. 9.57 kg/h of water with 100 ppm of EDA (N-MeEDA below the detection limit) are taken off overhead. At the bottom, 6.46 kg/h comprising 92 ppm of $H_2O$, 91.8% of EDA, 2.4% of N-MeEDA, 3.2% of DETA and 2.5% of other secondary components are taken off as mixture (G2).

The bottom output from D1 is fed into a column D2 in order to separate off N-MeEDA. The column D2 contains packing having 100 theoretical plates, of which 46 are in the stripping section and 54 are in the enrichment section. D2 is operated at a pressure at the top of 100 mbar. The pressure at the bottom is 115 mbar. The temperature at the top is 56.2° C., and the temperature at the bottom is 60.4° C. The amount of runback is 27.3 kg/h. 0.2 kg/h comprising 0.3% of $H_2O$, 24.9% of EDA and 74.8% of N-MeEDA is taken off overhead. At the bottom, 6.26 kg/h comprising 94.0% of EDA, 0.1% of N-MeEDA, 3.3% of DETA and 2.6% of other secondary components are taken off.

As can be seen from example 2, both $H_2O$ and N-MeEDA can be separated off virtually completely from EDA in the process of the invention, without an azeotropic distillation having to be carried out.

The invention claimed is:

1. A process for purifying ethylenediamine (EDA) by distillation, comprising a) and b):
   a) introducing a mixture (G1) comprising water, EDA and N-methylethylenediamine (N-MeEDA) into a distillation apparatus (D1), wherein
      i) a stream (S1) comprising water is distilled off overhead from (D1) at a pressure of greater than 4.8 bara and
      ii) a mixture (G2) depleted in water compared to the mixture (G1) is taken off from the bottom of (D1),
   b) introducing the mixture (G2) into a distillation apparatus (D2), wherein
      i) a stream (S2) comprising N-MeEDA is distilled off overhead from (D2) and
      ii) a stream (S3) depleted in N-MeEDA compared to the mixture (G2) is taken off from the bottom of (D2).

2. The process according to claim 1, wherein the mixture (G1) further comprises ammonia ($NH_3$) and the process further comprises removing of ammonia from the mixture (G1) c) and the removing c) is performed before the introducing of a mixture (G1) into a distillation apparatus (D1) a).

3. The process according to claim 2, wherein the removing of ammonia c) is two stages, comprising
   taking off ammonia overhead at from 20 to 70° C. from the mixture (G1) in a distillation apparatus (D3) and condensing, wherein the temperature at the bottom is less than 220° C. and a mixture (G1a) depleted in $NH_3$ is transferred from the bottom to a distillation apparatus (D4),
   separating off the mixture (G1b) from the bottom in the second distillation apparatus (D4), wherein the mixture (G1b) is completely or largely free of ammonia and the mixture (G1b) is fed instead of the mixture (G1) into the distillation apparatus (D1) in the introducing of a mixture a).

4. The process according to claim 1, wherein the EDA comprising the mixture (G1) is prepared by a process (A) or a process (B), wherein
   i) the process (A) comprises (A1) to (A3)
      A1) reacting formaldehyde and hydrocyanic acid (HCN) to form formaldehyde cyanohydrin (FACH), wherein the hydrocyanic acid is completely or largely free sulfur dioxide ($SO_2$),
      A2) reacting FACH with ammonia ($NH_3$) to form aminoacetonitrile (AAN),
      A3) hydrogenating AAN in the presence of a catalyst to form EDA,
   ii) the process (B) comprises (B1) and (B2):
      B1) reacting ethylene oxide (EO) with ammonia ($NH_3$) to form ethanolamine (EOA),
      B2) reacting EOA with $NH_3$ to form EDA.

5. The process according to claim 4, wherein the hydrogenating (A3) of the process (A) is carried out in the presence of a Raney catalyst.

6. The process according to claim 4, wherein the hydrogenating (A3) of the process (A) is carried out in the presence of a Raney nickel catalyst or a Raney cobalt catalyst.

7. The process according to claim 4, wherein the hydrogenating (A3) of the process (A) is carried out in the presence of a Raney cobalt catalyst comprising at least one selected from the group consisting of the elements Fe, Ni, and Cr as a promoter.

8. The process according to claim 4, wherein the mixture (G1) further comprises ammonia and the process further comprises removing of ammonia $NH_3$ from the mixture (G1) c) before the introducing of a mixture (G1) into a distillation apparatus (D1) a), wherein the ammonia is separated off in the removing of ammonia c) and recirculated to a preceding process step, wherein the ammonia recirculation is performed after the reacting formaldehyde cyanohydrin with ammonia A2) of the EDA preparing process (A) or after at least one of the reacting ethylene oxide with ammonia B1) or the reacting ethanolamine with ammonia B2) of the EDA preparing process (B).

9. The process according to claim 1, wherein the process further comprises d):
   d) introducing the stream (S3) into a distillation apparatus (D5), wherein EDA is distilled off overhead from D5 at a pressure of from 200 mbara to 2 bara and the EDA has a purity of at least 95%.

10. The process according to claim 9, wherein the EDA distilled off overhead has a purity of at least 99%.

11. The process according to claim 9, wherein the EDA distilled off overhead has a purity of at least 99.5%.

12. The process according to claim 1, wherein the mixture (G1) further comprises diethylenetriamine (DETA) and the process further comprises removing DETA e).

13. The process according to claim 9, wherein the mixture (G1) further comprises diethylenetriamine (DETA) and the process further comprises removing DETA e) performed after the introducing of the mixture (G2) into a distillation apparatus (D2) b) or after the introducing of the stream (S3) into a distillation apparatus (D5) d).

14. The process according to claim 13, wherein the stream (S3) comprises DETA and a stream (S4) enriched in DETA compared to the stream (S3) is taken off from the bottom of the distillation apparatus (D5) and the removing of DETA e) comprises:
   e) introducing the stream (S4) into a distillation apparatus (D6), wherein DETA is distilled off via a side offtake from D6.

15. The process according to claim 1, wherein, during the introducing of a mixture (G1) into a distillation apparatus (D1) a), the temperature at the bottom of the distillation apparatus (D1) is from 175 to 250° C. or wherein the water comprising the mixture (G1) is completely or largely distilled off overhead from (D1).

16. The process according to claim 1, wherein the mixture (G2) taken off from the bottom of the distillation apparatus (D1) in the introducing of a mixture (G1) into a distillaapparatus (D1) a) comprises less than 1000 ppm by weight of water relative to the total weight of the mixture (G2).

17. The process according to claim 1, wherein the mixture (G2) taken off from the bottom of the distillation apparatus (D1) in the introducing of a mixture (G1) into a distillation apparatus (D1) a) comprises less than 200 ppm by weight of water relative to the total weight of the mixture (G2).

18. The process according to claim 1, wherein the mixture (G2) taken off from the bottom of the distillation apparatus (D1) in the introducing of a mixture (G1) into a distillation apparatus (D1) a) comprises less than 50 ppm by weight of water relative to the total weight of the mixture (G2).

19. The process according to claim 1, wherein the distillation apparatus (D2) in the introducing of the mixture (G2) into a distillation apparatus (D2) b) is operated at a temperature at the bottom of from 20 to 75° C. or at a pressure at the top of from 10 to 500 mbara.

20. The process according to claim 1, wherein the distillation apparatus (D2) in the introducing of the mixture (G2) into a distillation apparatus (D2) b) is operated at a pressure at the top of from 50 to 200 mbara.

21. The process according to claim 1, wherein the stream (S3) taken off from the bottom of the distillation apparatus (D2) in the introducing of the mixture (G2) into a distillation apparatus (D2) b) comprises less than 10000 ppm by weight of N-MeEDA relative to the total weight of the stream (S3).

22. The process according to claim 1, wherein the stream (S3) taken off from the bottom of the distillation apparatus (D2) in the introducing of the mixture (G2) into a distillation apparatus (D2) b) comprises less than 1000 ppm by weight of N-MeEDA relative to the total weight of the stream (S3).

23. The process according to claim 1, wherein the stream (S3) taken off from the bottom of the distillation apparatus (D2) in the introducing of the mixture (G2) into a distillation apparatus (D2) b) comprises less than 200 ppm by weight of N-MeEDA relative to the total weight of the stream (S3).

24. The process according to claim 1, wherein the stream (S2) distilled off overhead from the distillation apparatus (D2) in the introducing of the mixture (G2) into a distillation apparatus (D2) b) comprises from 20 to 50 ppm by weight of EDA relative to the total weight of the stream (S2).

25. The process according to claim 1, wherein the stream (S2) distilled off overhead from the distillation apparatus (D2) in the introducing of the mixture (G2) into a distillation apparatus (D2) b) comprises from 22 to 40 ppm by weight of EDA relative to the total weight of the stream (S2).

26. The process according to claim 1, wherein the stream (S2) distilled off overhead from the distillation apparatus (D2) in the introducing of the mixture (G2) into a distillation apparatus (D2) b) comprises from 23 to 30 ppm by weight of EDA relative to the total weight of the stream (S2).

27. The process according to claim 1, wherein the mixture (G1) comprises at least 99% by weight of at least one selected from the group consisting of, EDA, N-MeEDA, DETA, water and $NH_3$ relative to the total weight of the mixture (G1).

28. The process according to claim 1, wherein the mixture (G1) comprises of at least 99.5% by weight of at least one selected from the group consisting of, EDA, N-MeEDA, DETA, water and $NH_3$ relative to the total weight of the mixture (G1).

* * * * *